United States Patent [19]

Harris et al.

[11] 3,931,235
[45] Jan. 6, 1976

[54] PROCESS FOR PREPARING SULFUR-CONTAINING HYDROXY PYRONES

[75] Inventors: Robert F. Harris; Joseph E. Dunbar, both of Midland, Mich.

[73] Assignee: The Dow Chemical Company, Midland, Mich.

[22] Filed: Dec. 28, 1973

[21] Appl. No.: 429,313

Related U.S. Application Data

[62] Division of Ser. No. 316,240, Dec. 18, 1972, Pat. No. 3,818,046.

[52] U.S. Cl. .............................................. 260/343.5
[51] Int. Cl.² ....................................... C07D 309/38
[58] Field of Search ................................. 260/343.5

[56] References Cited
OTHER PUBLICATIONS

Theilheimer, Synthetic Methods of Organic Chemistry, 25, p. 345 (1971).

*Primary Examiner*—Lorraine A. Weinberger
*Assistant Examiner*—E. Jane Skelly
*Attorney, Agent, or Firm*—Theodore Post; C. Kenneth Bjork

[57] ABSTRACT

This invention concerns sulfur-containing hydroxy pyrones corresponding to the formula

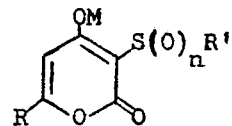

wherein M is H or alkali metal, R is methyl, R' is hydrogen, alkyl, phenyl, halophenyl, nitrophenyl, loweralkylphenyl, benzyl, phenethyl, naphthylmethyl, halobenzyl, loweralkylbenzyl, nitrobenzyl, propargyl, allyl, cyclohexyl loweralkyl, (loweralkylthio)-loweralkyl or adamantyl and n is 0 to 2. The compounds are prepared by reacting the mono-alkali metal salt of 4-hydroxy-6-methyl-2-pyrone with an appropriate thiosulfonate, advantageously in the presence of an organic solvent. The compounds have utility as plant growth stunters and as antimicrobial agents.

1 Claim, No Drawings

PROCESS FOR PREPARING SULFUR-CONTAINING HYDROXY PYRONES

CROSS-REFERENCE TO RELATED APPLICATION

This is a division of application Ser. No. 316,420, filed Dec. 18, 1972, now U.S. Pat. No. 3,818,046.

SUMMARY OF THE INVENTION

This invention concerns sulfur-containing hydroxy pyrones and their alkali metal salts corresponding to the formula

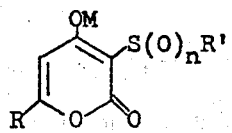

wherein M represents hydrogen or alkali metal, R represents methyl, R' represents hydrogen, a 1 to 20 carbon alkyl, phenyl, halophenyl, nitrophenyl, lower alkylphenyl, benzyl, phenethyl, naphthylmethyl, halobenzyl, lower alkylbenzyl, nitrobenzyl, propargyl, allyl, cyclohexyl lower alkyl, (lower alkylthio)-lower alkyl or adamantyl, and n represents an integer from 0 to 2. In the specification and claims, "lower alkyl" designates a straight or branched chain alkyl group such as, for example, methyl, ethyl, propyl, isopropyl, butyl, isobutyl, secondary butyl or tertiary butyl and halo designates fluoro, chloro or bromo.

The compounds are prepared in the following several ways.

1. Process for the simultaneous preparation of a 3-sulfenylated-4-hydroxy-6-methyl-2-pyrone and a sulfinic acid

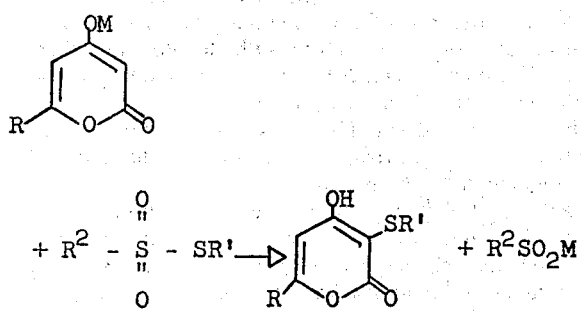

A mixture of the mono-alkali metal salt of 4-hydroxy-6-methyl-2-pyrone and substantially one molar equivalent of the appropriate thiolsulfonate in an inert organic solvent, i.e., methanol, ethanol, acetonitrile, 2-propanol, benzene, toluene, methyl ethyl ketone, acetone or methyl isobutyl ketone is heated at substantially reflux temperature with agitation for about 30 minutes to about 24 hours. The solvent is removed by distillation in vacuo and the residue extracted with water. The crude pyrone product is collected on a filter. The filtrate is acidified with a mineral acid, such as sulfuric or hydrochloric acid to precipitate the sulfinic acid which is removed by filtration and dried. The crude pyrone product is purified by crystallization from an appropriate solvent such as methanol, ethanol, 2-propanol, nitromethane, acetonitrile, benzene, hexane, cyclohexane, methylcyclohexane, acetone, methyl ethyl ketone or methyl isobutyl ketone or any combination of the foregoing solvents.

In an alternative procedure the 4-hydroxy-6-methyl-2-pyrone is dissolved in a solution of water and a substantially molar equivalent of an alkali metal hydroxide. To this solution is then added a molar equivalent of the appropriate thiolsulfonate, and the resulting mixture is heated under reflux with agitation (shaking or stirring) for a period of time necessary for completion of the reaction (i.e., about 30 minutes to about 24 hours). The mixture is then cooled to ambient temperature and extracted with an appropriate solvent such as chloroform, methylene chloride, carbon tetrachloride, 1,1,1-trichloroethane, ethyl ether, benzene, toluene, xylene or mixed liquid chlorinated hydrocarbons. The extract is dried over an appropriate drying agent such as anhydrous sodium sulfate, anhydrous magnesium sulfate or anhydrous calcium sulfate, and the solvent is removed either by evaporation or by distillation at a convenient pressure (i.e., 760 to 0.1 mm Hg), depending on the nature of the solvent. The product residue may not require further purification, or it may be further purified by crystallization from an appropriate solvent, as shown above.

2. Process for the sulfenylation of 4-hydroxy-6-methyl-2-pyrone with sulfenyl chlorides

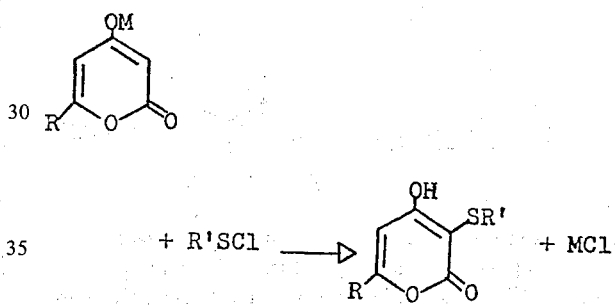

A solution of the appropriate alkane- or arenesulfenyl chloride in an inert organic solvent, i.e., methylene chloride, chloroform, carbon tetrachloride, benzene, 1,1,1-trichloroethane or mixed chlorinated hydrocarbons, is added to a slurry of a substantially molar equivalent of the mono-alkali metal salt of 4-hydroxy-6-methyl-2-pyrone in the same solvent over a period of about 5 minutes to about one hour, keeping the temperature rise under control (for example: below 25°C.) by means of a cooling bath. The reaction mixture is then stirred at ambient temperature for about 30 minutes to about 24 hours. The solvent is then removed either by evaporation or by distillation at a convenient pressure (i.e., 760 to 0.1 mm Hg), depending on the nature of the solvent. The residue is then triturated with water to remove the by-product alkali metal chloride and is collected on a filter and dried. The product thus obtained may be used without further purification, or it may be further purified by recrystallization from an appropriate solvent, such as methanol, ethanol, 2-propanol, nitromethane, acetonitrile, benzene, hexane, cyclohexane, methylcyclohexane, acetone, methyl ethyl ketone or methyl isobutyl ketone or any combination of the foregoing solvents.

In an alternative procedure, the appropriate alkane- or arenesulfenyl chloride dissolved in an inert solvent, such as methylene chloride, chloroform, carbon tetrachloride, benzene, 1,1,1-trichloroethane or mixed liquid chlorinated hydrocarbon solvents, is added to a vigorously agitated suspension or solution of 4-hydroxy-6-methyl-2-pyrone in the same solvent, and the mixture heated at substantially reflux temperature for a period of time necessary for completion of the reaction as determined by the cessation of the evolution of the hydrogen chloride gas by-product. The mixture is then cooled; and, in cases where the product separates under these conditions, said product is collected on a filter and dried. In cases where the product does not separate from the solvent, the solution is either concentrated to cause separation of the product, or the solvent is removed by evaporation or by distillation at an appropriate pressure (i.e., 760 to 0.1 mm Hg), depending on the nature of the solvent. The crude product may be used without further purification, or it may be further purified as shown above.

3. Preparation of 3-sulfenylated-4-hydroxy-6-methyl-2-pyrones from 4-hydroxy-3-mercapto-6-methyl-2-pyrone and halide alkylating agents ($S_{n2}$ route)

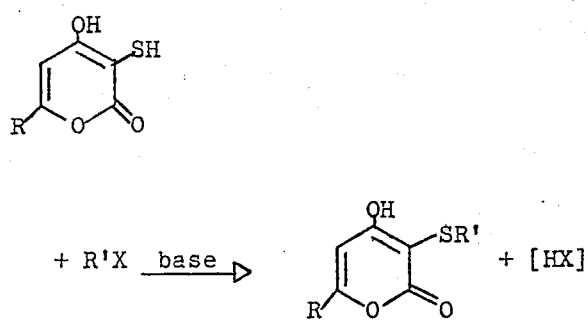

To a solution of 4-hydroxy-3-mercapto-6-methyl-2-pyrone in pyridine at a temperature of from about -5 to about 35°C. is added the appropriate alkyl halide with ice bath cooling when necessary. After the addition is complete, the reaction mixture is heated to about 80° to 90°C. for about 15 minutes to about one hour, or not heated at all, and allowed to stand at room temperature for about one to about 24 hours. After the reaction period, the mixture is poured into a mixture of ice and excess mineral acid, such as sulfuric or hydrochloric acid, and the crude product is separated either by filtration or by extraction with an appropriate solvent such as methylene chloride, ethyl ether, benzene, toluene, chloroform or 1,1,1-trichloroethane.

In cases where the crude product is crystalline, insoluble in the aqueous mixture and filterable, it is dried and purified by recrystallization (sometimes accompanied by the use of activated charcoal) from an appropriate solvent such as methanol, ethanol, 2-propanol, nitromethane, acetonitrile, benzene, hexane, cyclohexane, methylcyclohexane, acetone, methyl ethyl ketone or methyl isobutyl ketone or any combination of the foregoing solvents.

In cases where it is necessary to extract the crude product from the aqueous mixture, the extract is dried over an appropriate drying agent such as anhydrous sodium sulfate, anhydrous magnesium sulfate or anhydrous calcium sulfate, and the solvent is removed either by evaporation or by distillation at a convenient pressure (i.e., 760 to 0.1 mm Hg), depending on the nature of the solvent. The product may not require further purification, or it may be further purified as above.

4. Preparation of 3-sulfenylated-4-hydroxy-6-methyl-2-pyrones from 4-hydroxy-3-mercapto-6-methyl-2-pyrone and tert.-alcohols ($S_{n2}$ - route)

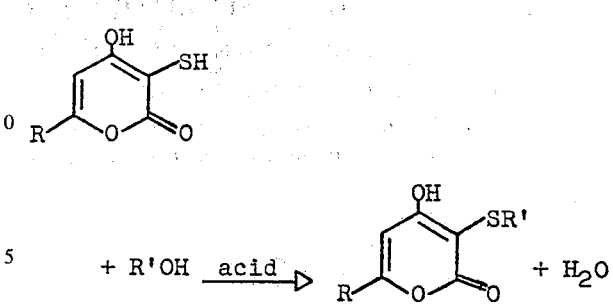

Ice is slowly added with stirring to concentrated sulfuric acid (preferably one part ice to 3.5 parts sulfuric acid), keeping the temperature at a moderate degree (preferably below 35°C.) by means of a cooling bath. The temperature of the diluted acid is adjusted to about 5°C., and an excess (preferably about two molar equivalents of alcohol to one of pyrone) of the tertiary alcohol is slowly added with stirring, keeping the temperature at a moderate degree (preferably between 5° and 10°C.). 4-Hydroxy-3-mercapto-6-methyl-2-pryone is then added with vigorous stirring over a period of about 15 minutes, keeping the temperature of the reaction mixture at or below 5°C. The reaction mixture is then allowed to come to ambient temperature and is allowed to remain at that temperature for about 10 minutes to about 24 hours, after which period of time it may be heated to from 30° to 50°C. for from 1 to 5 hours and is then poured into ice water. The crude product is purified by usual crystallization procedures (see above) or it may be dissolved in aqueous sodium hydroxide solution (preferably 3 to 5 percent) and the solution stirred at room temperature with decolorizing charcoal, filtered and acidified with mineral acid to give the solid product, which is collected on a filter, washed with water and dried. The crude product can be used without further purification or it can be further purified by recrystallization, as above.

Allyl- and propargylthiopyrones can be prepared by foregoing process 1 and process 3 but not by process 2, as allyl- and propargylsulfenyl chlorides do not exist and cannot be made by known procedures.

Process 3 or process 4 must be used when only alkylating agents R'X or R'OH, respectively, are available in the absence of the availability of the corresponding thiolsulfonate and/or sulfenyl chloride.

It is more convenient to use process 1 over process 2 in cases where the latter would require the use of a sulfenyl chloride with one or two alpha hydrogen atoms, since said sulfenyl chlorides must be prepared at low (ca. −40°C.) temperatures to avoid chlorination of the alpha carbon atom.

Process 2 is preferred in cases where the particular intermediate sulfenyl chloride is made more conveniently than the corresponding thiolsulfonate such as in the synthesis of 3-arylthiopyrones. Of the four processes, only processes 1 and 2 can be used for the introduction of arylthio groups in the 3-position.

Process 4 is preferred in cases where R'S is a bulky group and where $R'^{+}$ represents an abnormally stable carbonium ion, permitting a facile $S_{nl}$ attack on the sulfur atom.

DESCRIPTION OF SOME PREFERRED EMBODIMENTS

The following examples illustrate the present invention and the manner and process of making and using it, setting forth the best mode contemplated by the inventors of carrying out the invention. The examples should not be construed as limitations upon the overall scope of the invention. Temperature is given in Centigrade degrees.

EXAMPLE 1

4-Hydroxy-6-methyl-3-methylthio-2-pyrone

A mixture of the monosodium salt of 4-hydroxy-6-methyl-2-pyrone (14.8 g., 0.100 mol), methyl p-toluenethiolsulfonate (20.2 g., 0.100 mol), and 2B absolute ethanol (250 ml.) was heated at reflux for 21 hours. The ethanol was removed by distillation in vacuo; on attempted trituration with water (200 ml.), an oil separated. The oil was removed and the aqueous phase extracted with chloroform (2 × 100 ml.). The oil and chloroform washings were combined, dried over anhydrous $Na_2SO_4$, and the chloroform removed by distillation in vacuo. The resulting solid product, 4.5 g. (m. 130°–136°C., 26% yield) was twice recrystallized from 2-propanol to obtain the pure product, m. 141°–141.5°. The aqueous layer was acidified with dilute HCl producing 10.0 g. (64 percent yield) of the by-product p-toluenesulfinic acid, m. 79°–85°C.

Anal. Calcd. for $C_7H_8O_3S$: C, 48.8; H, 4.68; S, 18.5. Found: C, 49.0; H, 4.86; S, 18.3.

EXAMPLE 2

4-Hydroxy-6-methyl-3-methylthio-2-pyrone

Methanesulfenyl chloride (21.6 g., 0.261 mol) dissolved in methylene chloride (100 ml.) was added to a rapidly stirred slurry of the monosodium salt of 4-hydroxy-6-methyl-2-pyrone (38.6 g., 0.261 mol) in methylene chloride (500 ml.) over a period of 35 minutes. The reaction temperature was maintained at 25°C. with cooling during the addition; then stirring was continued at ambient temperature for 4 hours. The methylene chloride was removed by distillation in vacuo and the residue triturated with water (200 ml.) to remove the by-product sodium chloride. The crude product was removed by filtration, 26.0 g., m. 127°–134°C., 58 percent yield; after recrystallization from 2-propanol, 17.2 g., m. 139°–140.5°C., 38 percent yield

EXAMPLE 3

4-Hydroxy-6-methyl-3-methylthio-2-pyrone

A mixture of 47.0 g. (0.317 mole) of the monosodium salt of 4-hydroxy-6-methyl-2-pyrone and 40.0 g. (0.317 mole) of methyl methanethiolsulfonate in 700 ml. of 2B absolute ethanol was heated under reflux with stirring for four hours. The solvent was then removed by evaporation in vacuo, leaving a viscous semi-solid. The crude substance was washed with water and extracted with methylene chloride. The combined extracts were dried over anhydrous sodium sulfate and evaporated in vacuo to dryness, leaving 24.8 g. of a yellow solid; which, when recrystallized from isopropanol gave 10.6 g. (20 percent) of the pure product m. 141.5°–143°C.

EXAMPLE 4

4-Hydroxy-6-methyl-3-phenylthio-2-pyrone

A mixture of the monosodium salt of 4-hydroxy-6-methyl-2-pyrone (28.3 g., 0.191 mol), phenyl benzenethiolsulfonate (47.7 g., 0.191 mol), and 2B absolute ethanol (500 ml.) was heated at reflux with stirring for 6 hours. The ethanol was removed by distillation in vacuo and the residue triturated with water (350 ml.). The crude product was removed by filtration, 43.0 g. (m. 142°–165°C., 80 percent purity, 77 percent yield); acidification of the filtrate with dilute HCl produced additional product, 6.9 g. (m. 160°–165°C., 92 percent total yield). Recrystallization from 2-propanol gave 30.0 g., m. 163°–165°C., 67 percent yield. A second recrystallization from 2-propanol gave the pure product, m. 164.5°–165.5°C. Evaporation of the aqueous filtrate (to 50 ml.) gave 14.8 g. (55 percent yield) of the by-product benzenesulfinic acid, m. 81°–85°C.

Anal. Calcd. for $C_{12}H_{10}O_3S$: C, 61.5; H, 4.30; S, 13.7. Found: C, 61.3; H, 4.34; S, 13.4.

EXAMPLE 5

4-Hydroxy-6-methyl-3-phenylthio-2-pyrone

4-Hydroxy-6-methyl-2-pyrone (6.3 g., 0.050 mol) was dissolved in a solution of sodium hydroxide (2.0 g., 0.050 mol) and water (150 ml.). Phenyl benzenethiolsulfonate (12.5 g., 0.050 mol) was added and the mixture heated at reflux for 6 hours. An oil resulted which was extracted with chloroform (2 × 100 ml.). The chloroform solution was dried over anhydrous sodium sulfate, filtered, and the chloroform removed by distillation in vacuo. The resulting solid product was washed with 2-propanol, 3.2 g. colorless crystals, m. 164°–165.5°C., 27 percent yield.

EXAMPLE 6

4-Hydroxy-6-methyl-3-phenylthio-2-pyrone

Benzenesulfenyl chloride (7.2 g., 0.050 mol) dissolved in benzene (15 ml.) was added to a rapidly stirred slurry of the monosodium salt of 4-hydroxy-6-methyl-2-pyrone (7.4 g., 0.050 mol) in benzene (110 ml.) over a period of 12 minutes. The reaction temperature was maintained at 25°–27°C. with cooling during the addition; then the reaction mixture was heated at reflux for 30 minutes. The benzene was removed by distillation in vacuo and the residue triturated with water (100 ml.) to remove the by-product sodium chloride. The crude product was removed by filtration, 10.9 g., m. 158°–163°C., 93 percent yield. A portion was recrystallized from ethanol, m. 164.5°–165.5°C. Evaporation of the aqueous filtrate to dryness in vacuo produced 2.9 g. (100 percent yield) of the by-product sodium chloride.

EXAMPLE 7

4-Hydroxy-6-methyl-3-phenylthio-2-pyrone

Benzenesulfenyl chloride (7.2 g., 0.050 mol) dissolved in benzene (15 ml.) was added to a rapidly stirred slurry of 4-hydroxy-6-methyl-2-pyrone (6.3 g., 0.050 mol) in benzene (135 ml.). There was no apparent reaction at ambient temperature, but upon heating hydrogen chloride was evolved. After heating at reflux for 2 hours, the mixture was cooled and filtered to give 11.6 g. colorless crystals, m. 160°–162.5°C., 99 percent yield.

EXAMPLE 8

3-p-Chlorophenylthio-4-hydroxy-6-methyl-2-pyrone

A mixture of the monosodium salt of 4-hydroxy-6-methyl-2-pyrone (29.6 g., 0.200 mol), p-chlorophenyl p-toluenethiolsulfonate (59.8 g., 0.200 mol), and 2B absolute ethanol (500 ml.) was heated at reflux with stirring for 6.5 hours. The ethanol was removed by distillation in vacuo and the residue triturated with water (300 ml.). The crude product was removed by filtration, 53.0 g. (m. 166°–177°C., 91% yield); after recrystallization from ethanol, 36.4 g., m. 175°–180°C., 68% yield. A second recrystallization produced the pure product, 18.0 g., m 181°–182°C., 34 percent yield. The aqueous filtrate was acidified with dilute HCl producing 21.8 g. (70 percent yield) of the by-product p-toluenesulfinic acid, m. 87°–89°C.

Anal. Calcd. for $C_{12}H_9ClO_3S$: C, 53.6; H, 3.38; S, 11.9. Found: C, 53.6; H, 3.46; S, 12.0.

EXAMPLE 9

3-Benzylthio-4-hydroxy-6-methyl-2-pyrone

A mixture of the monosodium salt of 4-hydroxy-6-methyl-2-pyrone (20.2 g., 0.136 mol), benzyl p-toluenesulfonate (37.8 g., 0.136 mol), and 2B absolute ethanol (340 ml.) was heated at reflux with stirring for 5 hours. The ethanol was removed by distillation in vacuo and the residue triturated with water (250 ml.). The crude product was removed by filtration, 32.6 g. (m. 104°–120°C., 92 percent purity, 89 percent yield); after recrystallization from 2-propanol, 18.7 g., m. 124°–129°C., 55% yield. A second recrystallization from 2-propanol gave the pure product as colorless crystals, m. 128°–129°C. The aqueous filtrate was acidified with dilute HCl producing 14.0 g. (66 percent yield) of the by-product p-toluenesulfinic acid, m. 83°–86°C.

Anal. Calcd. for $C_{13}H_{12}O_3S$: C, 62.9; H, 4.87; S, 12.9 Found: C, 62.7; H, 4.82; S, 12.7.

EXAMPLE 10

3-Dodecylthio-4-hydroxy-6-methyl-2-pyrone

A mixture of 21.6 g. (0.145 mole) of the monosodium salt of 4-hydroxy-6-methyl-2-pyrone and 52.0 g. (0.145 mole) of n-dodecyl p-toluenethiolsulfonate in 400 ml. of 2B absolute ethanol was heated at reflux with stirring for 22 hours. The ethanol was removed by evaporation in vacuo, and the solid residue was stirred with 400 ml. of water. The aqueous suspension was then extracted with methylene chloride and the extract dried over anhydrous magnesium sulfate. The methylene chloride was removed by evaporation in vacuo, and the sticky, semi-solid residue was triturated with n-hexane to give the pure product as 22.7 g. (48 percent) of a white solid, m. 77.5°–78.5°C.

Anal. Calcd. for $C_{18}H_{30}O_3S$: C, 66.22; H, 9.26; S, 9.82. Found: C, 66.2; H, 9.18; S, 9.8.

EXAMPLE 11

3-(2,4-Dinitrophenylthio)-4-hydroxy-6-methyl-2-pyrone 2,4-Dinitrobenzenesulfenyl chloride (23.5 g., 0.100 mole) was added to a slurry of 12.6 g. (0.100 mole) of 4-hydroxy-6-methyl-2-pyrone in 150 ml. of methylene chloride, containing 10 ml. (0.125 mole) of pyridine. An exothermic reaction occurred, causing the methylene chloide to reflux gently. After the mixture had been stirred at room temperature for one hour the precipitated yellow solid product was collected on a filter, washed with water and dried in vacuo. This crop weighed 17.4 g., m.p. 262°C. (dec.). A second crop of yellow solid (wt. 13.4 g., m.p. 210°C.) was obtained by evaporation of the filtrate. The two combined crops were recrystallized from a mixture of dimethylformamide and isopropanol to give 23.1 g. (71 percent) of the product 3-(2,4-dinitrophenylthio)-4-hydroxy-6-methyl-2-pyrone as yellow crystals, m.p. 270°C. (dec.).

EXAMPLE 12

3-Ethylthio-4-hydroxy-6-methyl-2-pyrone

A mixture of 37.2 g. (0.295 mole) of 4-hydroxy-6-methyl-2-pyrone and 28.4 g. (0.295 mole) of ethanesulfenyl chloride in 900 ml. of toluene was heated under reflux with stirring at 75°C. for two hours, during which time hydrogen chloride evolved. The reaction mixture was cooled to room temperature and filtered to remove 24.2 g. of a solid (m. 170°–172°C. - probably a mixture of starting pyrone and an unknown substance). The filtrate was concentrated to give 13.3 g. (25 percent) of the product as a white solid, m. 94°–95°C. Recrystallization from cyclohexane gave the pure product as white crystals, m. 101°–102°C.

Anal. Calcd. for $C_8H_{10}O_3S$: C, 51.59; H, 5.41; S, 17.22. Found: C, 51.4; H, 5.49; S, 16.65.

EXAMPLE 13

3-Isopropylthio-4-hydroxy-6-methyl-2-pyrone

A solution of 62.7 g. (0.57 mole) of isopropanesulfenyl chloride in 300 ml. of methylene chloride was added dropwise to a suspension of 84.5 g. (0.57 mole) of 4-hydroxy-6-methyl-2-pyrone in 200 ml. of methylene chloride while the reaction mixture was maintained at 20°C. The mixture was then warmed to 40°C. for 1.5 hours and finally stirred at room temperature for 17 hours. The by-product sodium chloride was removed by filtration and the filtrate evaporated to dryness, leaving a red liquid (85.5 g.) which solidified upon cooling in an ice bath. The crude product was recrystallized from cyclohexane to give 33.1 g. (28 percent) of the product as off-white crystals, m. 89°–91°C. A second recrystallization from cyclohexane gave white crystals, m. 91°–92°C.

Anal. Calcd. for $C_9H_{12}O_3S$: C, 53.93; H, 6.04; S, 16.01. Found: C, 54.1; H, 6.20; S, 15.9.

EXAMPLE 14

4-Hydroxy-6-methyl-3-[2-(methylthio)ethylthio]-2-pyrone

A solution of 8.0 g. (0.20 mole) of sodium hydroxide in 200 ml. of water was added to a stirred slurry of 25.2 g. (0.200 mole) of 4-hydroxy-6-methyl-2-pyrone in 400 ml. of ethanol. 2-(Methylthio)ethyl methanethiolsulfonate (37.3 g., 0.200 mole) was then added, and the mixture was heated at reflux with stirring for three hours. The reaction mixture was then concentrated to 150 ml. by evaporation in vacuo, and the two-phase system was extracted with methylene chloride. The extract was dried over anhydrous magnesium sulfate, filtered, and the solvent removed by evaporation in vacuo, leaving a dark brown oil as residue. After standing at room temperature for 24 hours a solid crystallized from the oil and was collected on a filter and recrystallized from cyclohexane to give the product 4-hydroxy-6-methyl-3-[2-(methylthio)ethylthio]-2-pyrone as 13.2 g. (29 percent) of a tan solid, m.p. 81°–83°C. A second recrystallization gave the pure substance as a white, crystalline solid, m.p. 81.5°–82°C.

Anal. Calcd. for $C_9H_{12}O_3S_2$: C, 46.53; H, 5.21; S, 27.60. Found C, 46.7; H, 5.1; S, 27.7.

EXAMPLE 15

4-Hydroxy-6-methyl-3-(2-nitrophenylthio)-2-pyrone o-Nitrobenzenesulfenyl chloride (18.9 g., 0.100 mole) was added to a slurry of 14.8 g. (0.117 mole) of 4-hydroxy-6-methyl-2-pyrone in 200 ml. of methylene chloride, containing 10 ml. (0.125 mole) of pyridine, causing the temperature to rise to 35°C. Complete solution was affected initially, but as the solution was stirred at ambient temperature a precipitate formed. After the reaction mixture had been stirred at room temperature for two hours, the yellow precipitate was collected on a filter, washed first with water, then with methylene chloride and finally dried in vacuo over calcium chloride. The crude product was recrystallized from aqueous dimethylformamide to give 20.8 g. (75%) of 4-hydroxy-6-methyl-3-(2-nitrophenylthio)-2-pyrone as a light yellow, crystalline solid, m.p. 229°C. (dec.). A second recrystallization from aqueous dimethylformamide gave the pure substance as light yellow crystals, m.p. 235°C. (dec.).

Anal. Calcd. for $C_{12}H_9NO_5S$: C, 51.61; H, 3.25; S, 11.48. Found: C, 51.5; H, 3.27; S, 11.2.

EXAMPLE 16

Ammonium Salt of 4-Hydroxy-6-methyl-3-phenylthio-2-pyrone

4-Hydroxy-6-methyl-3-phenylthio-2-pyrone (11.1 g., 0.0474 mol) and 15M aqueous ammonia (50 ml.) was stirred overnight at ambient temperature. The resultant solution was heated at reflux for 2 hours to strip the excess ammonia. The water was removed by distillation in vacuo; 50 ml. 2B absolute ethanol was added to the resultant gell and then removed by distillation in vacuo. The resultant light tan, crystalline product was dried overnight in a vacuum oven at 70°C., 8.8 g., m. 140°C. (dec.), 80 percent yield.

Anal. Calcd. for $C_{12}H_{13}NO_3S$: C, 57.35; H, 5.21; S, 12.7. Found: C, 57.7; H, 5.45; S, 12.7.

The ammonium salt of 4-hydroxy-6-methyl-3-phenylthio-2-pyrone (5.0 g., 0.0213 mol) was dissolved in water (50 ml.). Hydrochloric acid was added in excess and the 4-hydroxy-6-methyl-3-phenylthio-2-pyrone removed by filtration, 4.1 g., m. 164°–165°C., 83% yield.

EXAMPLE 17

3-Allylthio-4-hydroxy-6-methyl-2-pyrone

A mixture of 22.2 g. (0.150 mol) of sodium salt of 4-hydroxy-6-methyl-2-pyrone and 22.8 g. (0.100 mol) allyl-p-toluene thiolsulfonate in 150 ml. ethanol was heated at reflux for 3.5 hours. After cooling to room temperature, the reaction mixture was filtered to remove an off-white crystalline solid, mp>250°C. The filtrate was evaporated in vacuo to recover a solid residue. The solid was washed with water and extracted with methylene chloride. The extracts were dried ($Na_2SO_4$) and evaporated in vacuo to recover a yellow crystalline solid. One crystallization from cyclohexane gave the product as 7.2 g. (36 percent) of a light yellow solid. One additional recrystallization from cyclohexane gave the pure compound as a white crystalline solid, mp 98°–98.5°C.

Anal. Calcd. for $C_9H_{10}O_3S$: C, 54.53; H, 5.08; S, 16.17. Found: C, 54.5; H, 4.90; S, 16.0.

EXAMPLE 18

4-Hydroxy-3-isopentylthio-6-methyl-2-pyrone

To a slurry of 12.6 g. (0.100 mol) 4-hydroxy-6-methyl-2-pyrone in 100 ml. ethanol was added a solution of 4.0 g. (0.10 mol) NaOH in 50 ml. water. To the resulting clear solution was added 25.8 g. (0.100 mol) isopentyl-p-toluene thiolsulfonate. The mixture was heated at reflux temperature for 7 hours then stirred at room temperature overnight. After removing the solvent in vacuo, the residue was washed with water and extracted with methylene chloride. The extracts were dried ($Na_2SO_4$) and evaporated in vacuo to recover an oil which solidified upon cooling. The solid was recrystallized from cyclohexane (decolorized). To recover 12.4 g. (54 percent) of the desired product. One additional recrystallization from cyclohexane gave the pure compound, m.p. 81°–82°C.

Anal. Calcd. for $C_{11}H_{16}O_3S$: C, 57.87; H, 7.06; S, 14.04. Found: C, 58.0; H, 6.9; S, 13.9.

EXAMPLE 19

3-n-Hexylthio-4-hydroxy-6-methyl-2-pyrone

To a slurry of 37.9 g. (0.300 mol) 4-hydroxy-6-methyl-2-pyrone in 200 ml. ethanol was added a solution of 12 g. (0.30 mol) NaOH in 100 ml. water. To the resulting clear solution was added 54.7 g. (0.300 mol) n-hexylmethane thiolsulfonate. The reaction mixture was heated at reflux for 3 hours, then stirred at room temperature overnight. After removing the solvent in vacuo, the residue was slurried in water and extracted with methylene chloride. The extracts were dried ($Na_2SO_4$), and evaporated in vacuo to recover a solid. The solid was recrystallized from n-hexane to recover 40 g. (58 percent) of the pure product, m.p. 69°–70°C.

Anal. Calcd. for $C_{12}H_{18}O_3S$: C, 59.47; H, 7.48; S, 13.23. Found: C, 59.8; H, 7.68; S, 13.0

EXAMPLE 20

4-Hydroxy-6-methyl-3-(p-methylbenzylthio)-2-pyrone

An aqueous basic solution (8 g., 0.2 mol NaOH in 100 ml. $H_2O$) was added to a slurry of 4-hydroxy-6-methyl-2-pyrone (25.2 g., 0.200 mol) in 200 ml. ethanol. To the resulting clear solution was added p-methylbenzyl-p-toluene thiolsulfonate (58.5 g., 0.200 mol). The mixture was heated at reflux temperature for 5 hours then stored at room temperature over night. Evaporation of the reaction mixture to approximately 25 ml., then dilution with water, followed by extraction with methylene chloride, drying ($Na_2SO_4$), and evaporation of organic layer resulted in recovery of a light yellow solid. Solids were recrystallized from toluene to recover 24.9 g. (47 percent) of a white crystalline solid, m.p. 134°–135°C.

Anal. Calcd. for $C_{14}H_{14}O_3S$: C, 64.10; H, 5.38; S, 12.22. Found: C, 63.91; H, 5.32; S, 12.30.

EXAMPLE 21

3-(p-Chlorobenzylthio)-4-hydroxy-6-methyl-2-pyrone

To a slurry of 4-hydroxy-6-methyl-2-pyrone (25.2 g., 0.200 mol) in 200 ml. ethanol was added a basic solution (8.0 g., 0.20 mol NaOH in 100 ml. $H_2O$). To the resulting clear solution was added p-chlorobenzyl-p-toluene thiolsulfonate (62.4 g., 0.200 mol). The resulting mixture was heated at reflux temperature for 9 hours. After being stirred at room temperature over night, the mixture was evaporated in vacuo to dryness. The residue was dissolved in a mixture of $CHCl_3$—$H_2O$ and the organic layer was separated, dried ($Na_2SO_4$), and evaporated in vacuo to recover a light yellow solid. The solid was recrystallized from toluene to recover 27.4 g. (50 percent) of the desired compound, m.p. 139°–141°C.

Anal. Calcd. for $C_{13}H_{11}ClO_3S$: C, 55.22; H, 3.92; S, 11.34. Found: C, 55.6; H, 3.94; S, 11.2.

EXAMPLE 22

3-Cyclohexylmethylthio-4-hydroxy-6-methyl-2-pyrone

To a solution of 18.9 g. (0.150 mole) of 4-hydroxy-6-methyl-2-pyrone in 375 ml. of ethanol was added a solution of 6.0 g. (0.150 mole) of sodium hydroxide in 240 ml. of water followed by 42.7 g. (0.150 mole) of cyclohexylmethyl p-toluenethiolsulfonate. The reaction mixture was heated under reflux with stirring for 12 hours, after which period of time the solvent was removed by evaporation in vacuo, leaving a brown, mushy solid as residue. This was combined and shaken with water to remove the water-soluble by-product, sodium p-toluenesulfinate. This mixture was then extracted with methylene chloride, and the extract was dried over anhydrous magnesium sulfate. Removal of the solvent by evaporation in vacuo left a brown oil, which soon crystallized: weight 34.3 g. (90 percent). Recrystallization from a solution of benzene and petroleum ether (bp 60°–70°C.) gave 18.5 g. of cream colored solid, m.p. 80°–82°C. A second recrystallization gave the pure 3-cyclohexylmethylthio-4-hydroxy-6-methyl-2-pyrone as white crystals, m.p. 81.5°–83°C.

Anal. Calcd. for $C_{13}H_{18}O_3S$: C, 61.39; H, 7.13; S, 12.61. Found: C, 61.6; H, 7.48; S, 12.5.

EXAMPLE 23

Bis(4-hydroxy-6-methyl-2-oxo-3-pyranyl)-disulfide

Sulfur monochloride (13.5 g., 0.100 mole) was dissolved in 70 ml. of benzene, and the solution was added dropwise to a suspension of 25.2 g. (0.200 mole) of 4-hydroxy-6-methyl-2-pyrone in 500 ml. of benzene while the suspension was being heated under reflux with stirring. The addition was made over 25 minutes while hydrogen chloride was evolved and escaped through the condenser. The reaction mixture was heated under reflux with stirring for an additional one hour and 20 minutes, at the end of which period of time the evolution of hydrogen chloride had subsided. The light tan solid product (29.3 g., 93 percent) was collected on a filter and air dried; M.p. 225°C. (dec.). Recrystallization from nitromethane gave the pure bis(4-hydroxy-6-methyl-2-oxo-3-pyranyl)disulfide as cream colored platelets, m.p. 229°C. dec.

Anal. Calcd. for $C_{12}H_{10}O_6S_2$: C, 45.85; H, 3.21; S, 20.40. Found: C, 45.63; H, 3.28; S, 20.2.

This compound is an intermediate for preparation by the 3-mercapto $S_{n2}$ route. From it is prepared the compound of Example 28.

EXAMPLE 24

4-Hydroxy-6-methyl-3-propargylthio-2-pyrone

A solution of 39.5 g. (0.250 mole) of 4-hydroxy-3-mercapto-6-methyl-2-pyrone in 250 ml. of pyridine was cooled to 15°C. in an ice bath. Propargyl bromide (29.7 g., 0.250 mole) was then added in one portion, causing the temperature of the reaction mixture to rise to 53°C. When the temperature began to subside, the flask was placed on the steam bath and heated at 80°C. for one hour, during which pyridinium bromide by-product precipitated. The reaction mixture was then cooled and poured into a mixture of ice and 500 ml. of concentrated hydrochloric acid. After this mixture had been kept cold in an ice bath for one hour, the crystalline product, which formed, was collected on a filter and dried; m.p. 143.5°–146°C., weight 27.2 g. More product was obtained by extraction of the filtrate with methylene chloride, giving a total yield of 41.9 g., (85 percent). Two recrystallizations (Darco) from ethanol afforded the pure 4-hydroxy-6-methyl-3-propargylthio-2-pyrone as light tan crystals, m.p. 148°–149°C. (dec.).

Anal. Calcd. for $C_9H_8O_3S$: C, 55.09; H, 4.11; S, 16.34. Found: C, 54.9; H, 3.97; S, 16.03.

EXAMPLE 25

4-Hydroxy-6-methyl-3-(1-naphthylmethylthio)-2-pyrone

A solution of 15.8 g. (0.100 mole) of 4-hydroxy-3-mercapto-6-methyl-2-pyrone in 100 ml. of pyridine was cooled in an ice bath to about 15°C., and 17.7 g. (0.100 mole) of 1-chloromethylnaphthalene was added in one portion. The flask was then heated at 90°–95°C. on the steam plate for four hours. The reaction mixture was cooled and poured into 200 ml. of concentrated hydrochloric acid and about 400 g. of ice. A gummy solid was formed and was extracted with methylene chloride. The wet extract was treated with Darco and dried over anhydrous sodium sulfate. The solvent was removed by evaporation in vacuo, leaving a brown gum, which was crystallized (Darco) from ethanol to give 9.8 g. (33 percent) of tan crystals m.p. 155.5°–157.5°C. Recrystallization from ethanol gave the pure 4-hydroxy-6-methyl-3-(1-naphthylmethylthio)-2-pyrone as cream colored crystals, m.p. 169.5°–170.5°C.

Anal. Calcd. for $C_{17}H_{14}O_3S$: C, 68.44; H, 4.73; S, 10.75. Found: C, 68.3; H, 4.75; S, 10.66.

EXAMPLE 26

4-Hydroxy-6-methyl-3-(4-nitrobenzylthio)-2-pyrone

To a solution of 8.00 g. (0.0510 mole) of 4-hydroxy-3-mercapto-6-methyl-2-pyrone in 50 ml. of pyridine was added 11.0 g. (0.0510 mole) of p-nitrobenzyl bromide portionwise, keeping the temperature of the reaction mixture below 35°C. by means of an ice bath. After the addition was complete the reaction mixture was heated at 90°C. on the steam bath for two hours and 15 minutes. The mixture was then poured into ice and 100 ml. of concentrated hydrochloric acid. The cream colored solid precipitate was collected on a filter, washed with water and dried; m.p. 156°–160°C. (dec.), weight 12.2 g. (81 percent). Recrystallization from ethanol gave the pure 4-hydroxy-6-methyl-3-(4-nitrobenzylthio)-2-pyrone as tan crystals, m.p. 178°C.

Anal. Calcd. for $C_{13}H_{11}NO_5S$: C, 53.23; H, 3.78; N, 4.78. Found: C, 53.10; H, 3.86; N, 5.03.

EXAMPLE 27

3-(p-Fluorobenzylthio)-4-hydroxy-6-methyl-2-pyrone

To a stirred solution of 10.5 g. (0.0664 mole) of 4-hydroxy-6-methyl-3-mercapto-2-pyrone in 50 ml. of pyridine was added 9.60 g. (0.0664 mole) of p-fluorobenzyl chloride in one portion. The reaction was slightly exothermic, the temperature rising from 25° to 34°C. The reaction mixture was then allowed to stand at room temperature for four hours and at the end of this period was poured into a mixture of ice and 100 ml. of concentrated hydrochloric acid. The gummy precipitate was extracted with methylene chloride and the extract dried over anhydrous magnesium sulfate. The solvent was removed by evaporation in vacuo, leaving a light yellow oil, which crystallized upon cooling, weight 12.5 g. (71 percent). This was recrystallized from a solvent system of methylcyclohexane, benzene and ethanol to give light yellow crystals, m.p. 114.5°–118.5°C.; weight 7.20 g. Recrystallization from benzene gave the pure 3-(p-fluorobenzylthio)-4-hydroxy-6-methyl-2-pyrone as a pale yellow, crystalline solid, m.p. 118°–122°C.

Anal. Calcd. for $C_{13}H_{11}FO_3S$: C, 58.63; H, 4.16; S, 12.04. Found: C, 58.6; H, 4.12; S, 12.4.

EXAMPLE 28

4-Hydroxy-3-mercapto-6-methyl-2-pyrone

To a solution of 60.0 g. (1.50 moles) of sodium hydroxide and 78.6 g. (0.250 mole) of bis(4-hydroxy-6-methyl-2-oxo-3-pyranyl)disulfide in 750 ml. of water at 42°C. was added 47.9 g. (0.275 mole) of sodium hydrosulfite. The solution was allowed to stand for 30 minutes and then was acidified by the addition of concentrated hydrochloric acid, keeping the temperatures below 45°C. by the addition of a sufficient quantity of crushed ice. The precipitated, off-white solid was collected on a filter and dried in vacuo over calcium chloride for approximately 15 hours. The product weighed 76.3 g. (96 percent) and melted at 167°–169°C. (dec.). One recrystallization from methyl ethyl ketone gave the pure 4-hydroxy-3-mercapto-6-methyl-2-pyrone as light yellow crystals, m.p. 168°–169°C. (dec.).

Anal. Calcd. for $C_6H_6O_3S$: C, 45.56; H, 3.82; S, 20.27. Found: C, 45.58; H, 3.37; S, 20.3.

This compound is an intermediate for preparation by the 3-mercapto $S_{n2}$ route.

EXAMPLE 29

3-Benzylthio-4-hydroxy-6-methyl-2-pyrone

To a solution of 8.0 g. (0.051 mole) of 4-hydroxy-3-mercapto-6-methyl-2-pyrone in 38 ml. of pyridine was added 6.4 g. (0.051 mole) of benzyl chloride portionwise with stirring at room temperature. The reaction was slightly exothermic, the temperature rising from 23° to 30°C. The reaction mixture was stirred at room temperature for 30 minutes, and then heated on the steam bath for one hour at 90°–95°C. The reaction mixture was then cooled to room temperature and poured into a mixture of ice and 80 ml. of concentrated hydrochloric acid. The gummy precipitate, thus formed, was extracted with methylene chloride. The extract was dried over anhydrous sodium sulfate, filtered and evaporated to dryness to give 7.7 g. (61%) of brown oil, which was crystallized from toluene, containing a little methylcyclohexane, to give 5.0 g. of yellow-brown crystals, m.p. 117°–126°C. Recrystallization of this substance from toluene gave the pure 3-benzylthio-4hydroxy-6-methyl-2-pyrone as cream colored crystals, m.p. 127.5°–128.5°C.

EXAMPLE 30

α,α'-Bis(4-hydroxy-6-methyl-2-oxo-3-pyranylthio)-p-xylene

To a stirred solution of 15.8 g. (0.100 mole) of 4-hydroxy-3-mercapto-6-methyl-2-pyrone in 100 ml. of pyridine was added 8.75 g. (0.0500 mole) of α,α'-dichloro-p-xylene in one portion at room temperature. The reaction mixture was allowed to stand at room temperature for 15 hours and then was poured into a mixture of ice and 200 ml. of concentrated hydrochloric acid. The mixture was extracted with methylene chloride, leaving the methylene chloride-insoluble, white solid product behind. This was collected on a filter and found to weigh 5.3 g., m.p. 224°C. (dec.). The extract was dried over anhydrous sodium sulfate, and the methylene chloride was removed by evaporation in vacuo. The remaining 4.1 g. of light yellow solid residue was triturated with benzene containing a little ethanol, leaving 1.7 g. more product as an insoluble white solid, m.p. 228°–229°C. (dec.). Recrystallization of the combined product fractions from nitromethane gave the pure α,α'-bis(4-hydroxy-6-methyl-2-oxo-3-pyranylthio)-p-xylene as very pale yellow crystals, m.p. 234°C. (dec.).

Anal. Calcd. for $C_{20}H_{18}O_6S_2$: C, 57.40; H. 4.33; S, 15.32. Found: C, 57.1; H, 4.34; S, 15.2.

EXAMPLE 31

3-n-Dodecylsulfinyl-4-hydroxy-6-methyl-2-pyrone 3-n-Dodecylthio-4l-hydroxy-6-methyl-2-pyrone (9.8 g., 0.033 mol) was added to 30 ml. glacial acetic acid. A 30 percent solution of hydrogen peroxide (3.7 g., 0.033 mol) was added. After the mixture was stirred at room temperature for 0.5 hour, a clear solution was obtained. A white precipitate formed after one hour. Filtration of the material gave a solid: m.p. ~80°C. Additional solid formed in the filtrate after it was kept at room temperature overnight. The fractions were combined and dried to give 8.8 g. (84 percent) of the desired product. One recrystallization from cyclohexane gave the pure material as fluffy, white, crystalline needles: m.p. 79.5°–80.5°C.

Anal. Calcd. for $C_{18}H_{30}O_4S$: C, 63.12; H, 8.83; S, 9.36. Found: C, 63.35; H, 9.00; S, 9.5.

EXAMPLE 32

3-Benzylsulfinyl-4-hydroxy-6-methyl-2-pyrone

3-Benzylthio-4-hydroxy-6-methyl-2-pyrone (7.45 g., 0.0282 mol) and 30% hydrogen peroxide (3.7 g., 0.033 mol) were combined in 30 ml. glacial acetic acid and stirred at room temperature for 20 hours. The solution was then diluted with a mixture of toluene and ethanol (5:1) and warmed in vacuo to codistil the acetic acid. The recovered tan solid was recrystallized from toluene (DARCO) to give 5.4 g. (69 percent) of the desired product: m.p. 150°–153°C. One additional recrystallization from toluene gave the pure compound: m.p. 155°–156°C.

Anal. Calcd. for $C_{13}H_{12}O_4S$: C, 59.08; H, 4.58; S, 12.13. Found: C, 59.14; H, 4.4; S, 12.4.

EXAMPLE 33

3-Benzylthio-4-hydroxy-6-methyl-2-pyrone

3-Benzylthio-4-hydroxy-6-methyl-2-pyrone (7.45 g., 0.0266 mol), 30% hydrogen peroxide (10 g., 0.090 mol), and 50 ml. glacial acetic acid were combined and heated on a steam bath for 15 minutes. The clear solution was cooled, diluted with a mixture of toluene and ethanol (3.1) and warmed in vacuo to remove the acetic acid by codistillation, leaving 6.8 g. (81 percent) of white solid: m.p. 188°–190°C. The solid was recrystallized from cyclohexane, giving the pure substance as a fluffy white crystalline solid: m.p. 190°–191°C.

Anal. Calcd. for $C_{13}H_{12}O_5S$: C, 55.70; H, 4.32; S, 11.44 Found: C, 55.80; H, 4.33; S, 11.3.

EXAMPLE 34

3-n-Dodecylsulfonyl-4-hydroxy-6-methyl-2-pyrone 3-n-Dodecylthio-4-hydroxy-6-methyl-2-pyrone (9.8 g., 0.027 mol), 30% hydrogen peroxide solution (10 g., 0.090 mol), and 50 ml. glacial acetic acid were combined and heated on a steam bath for 15 minutes. After cooling to room temperature a precipitate began to form. The mixture was poured into 400 ml. of ice-water, and the crude product was collected on a filter and dried. The compound was recrystallized from cyclohexane to recover 8.8 g. (82 percent) of a white crystalline substance: m.p. 78°–79°C. A second recrystallization from cyclohexane gave the pure compound: m.p. 77°–78.5°C.

Anal. Calcd. for $C_{18}H_{30}O_5S$: C, 60.30, H, 8.44; S, 8.94. Found: C, 60.18; H, 8.1; S, 8.7.

EXAMPLE 35

3-Allylsulfinyl-4-hydroxy-6-methyl-2-pyrone

3-Allylthio-4-hydroxy-6-methyl-2-pyrone (5.95 g., 0.0300 mol), 30% hydrogen peroxide (3.85 g., 0.0330 mol), and 40 ml. glacial acetic acid were combined and stirred over night at room temperature. The clear solution was poured into 250 ml. ice water. The aqueous mixture was extracted with clhoroform. The CHCl₃ was dried ($Na_2SO_4$) and evaporated in vacuo. The recovered pink solid was recrystallized from cyclohexane-benzene to recover 5.0 g. (78 percent) of the desired compound. One additional recrystallization from cyclohexane-n-hexane gave the pure compound, m.p. 111°–112°C.

Anal. Calcd. for $C_9H_{10}O_4S$: C, 50.46; H, 4.70; S, 14.96. Found: C, 50.51; H, 4.81; S, 14.25.

EXAMPLE 36

4-Hydroxy-3-isopentylsulfinyl-6-methyl-2-pyrone

4-Hydroxy-3-isopentylthio-6-methyl-2-pyrone (4.5 g., 0.020 mol), 30% hydrogen peroxide (2.44 g., 0.0220 mol), and 35 ml. glacial acetic acid were combined and stirred over night at room temperature. The clear solution was diluted with a mixture of toluene and ethanol and the acetic acid was removed by codistillation in vacuo. A yellow liquid was recovered which solidified upon cooling. The compound was recrystallized from n-hexane to recover 2.5 g. (51 percent) of shiny yellow platelets. One additional recrystallization from n-hexane gave the pure compound as tiny white crystalline needles: m.p. 80°–81°C.

Anal. Calcd. for $C_{11}H_{16}O_4S$: C, 54.08; H, 6.02; S, 13.12. Found: C, 54.11; H, 6.42; S, 13.0.

EXAMPLE 37

3-n-Hexylsulfinyl-4-hydroxy-6-methyl-2-pyrone 3-n-Hexylthio-4-hydroxy-6-methyl-2-pyrone (9.1 g., 0.040 mol), 30% hydrogen peroxide (4.85 g., 0.0440 mol), and 40 ml. glacial acetic acid were combined and stirred at room temperature over night. The clear solution was poured into 200 ml. ice water and the resulting white precipitate was collected and dried in vacuo: m.p. 59°–60°C. The solid was recrystallized from n-hexane to recover 8.0 g. (77%) of the desired compound as white crystalline platelets, m.p. 59°–60°C.

Anal. Calcd. for $C_{12}H_{18}O_4S$: C, 55.79; H, 7.02; S, 12.41. Found: C, 56.0; H, 7.0; S, 12.6.

EXAMPLE 38

3-n-Hexylsulfonyl-4-hydroxy-6-methyl-2-pyrone 3-n-Hexylthio-4-hydroxy-6-methyl-2-pyrone (6.85 g., 0.0300 mol), 30% hydrogen peroxide (10.2 g., 0.0900 mol), and 40 ml. glacial acetic acid were combined and heated on a steam bath for 20 minutes. After cooling, the solution was poured into 200 ml. ice water and the resulting precipitate was collected and dried in vacuo. The compound was recrystallized from cyclohexane to recover 2.0 g. (25 percent) of the desired compound as white crystalline platelets, m.p. 65°–66°C.

Anal. Calcd. for $C_{12}H_{18}O_5S$: C, 52.54; H, 6.61; S, 11.69. Found: C, 52.5; H, 6.6; S, 11.2.

EXAMPLE 39

3-Isopentylsulfonyl-4-hydroxy-6-methyl-2-pyrone

3-Isopentylthio-4-hydroxy-6-methyl-2-pyrone (2.3 g., 0.10 mol), 30% hydrogen peroxide (4.8 g., 0.042 mol), and 35 ml. glacial acetic acid were combined and heated on a steam bath for 20 minutes. After cooling, the solution was poured into 200 ml. ice water. The precipitate was collected and dried in vacuo. The solid was recrystallized from cyclohexane to recover 1.4 g. (54 percent) of white crystalline flakes, m.p. 101°–102°C.

Anal. Calcd. for $C_{11}H_{16}O_5S$: C, 50.75; H, 6.20; S, 12.32. Found: C, 51.15; H, 6.53; S, 12.45.

EXAMPLE 40

4-Hydroxy-6-methyl-3-(p-methylbenzylsulfinyl)-2-pyrone

4-Hydroxy-6-methyl-3-(p-methylbenzylthio)-2-pyrone (10.5 g., 0.0400 mol), 30% hydrogen peroxide (5.14 g., 0.0440 mol), and 50 ml. glacial acetic acid were combined and stirred at room temperature for 20 hours. The reaction mixture was poured into 250 ml. ice-water and the recovered white precipitate was collected and dried. The solids were recrystallized from toluene to give 3.9 g. (35 percent) of the desired compound as a pale pink crystalline solid, m.p. 156°–158°C.

Anal. Calcd. for $C_{14}H_{14}O_4S$: C, 60.41; H, 5.07; S, 11.52. Found: C, 60.95; H, 4.94; S, 11.4.

EXAMPLE 41

3-(p-Chlorobenzylsulfinyl)-4-hydroxy-6-methyl-2-pyrone 3-p-Chlorobenzylthio-4-hydroxy-6-methyl-2-pyrone (11.3 g., 0.0400 mol), 30% hydrogen peroxide (5.14 g., 0.0440 mol) and 50 ml. glacial acetic acid were combined and stirred at room temperature for 4 hours. Then stored at room temperature over night. The reaction mixture, containing a crystalline solid, was added to 200 ml. of icewater. The precipitate was collected and dried. The solids were recrystallized from a mixture of cyclohexane-toluene to recover 8.6 g. (72 percent) of the desired compound, m.p. 150°–151°C. One additional recrystallization from cyclo-hexane-toluene gave the pure compound as white platelets, m.p. 151°–152°C.

Anal. Calcd. for $C_{13}H_{11}ClO_4S$: C, 52.26; H, 3.71; S, 10.73. Found: C, 52.36; H, 3.79.

EXAMPLE 42

4-Hydroxy-6-methyl-3-propargylsulfinyl-2-pyrone

To a suspension of 23.1 g. (0.124 mole) of 4-hydroxy-6-methyl-3-propargylthio-2-pyrone in 200 ml. of glacial acetic acid was added 14.1 g. (0.124 mole) of 30% hydrogen peroxide in 50 ml. of glacial acetic acid dropwise over a period of 20 minutes. The reaction mixture was stirred at room temperature for approximately 60 hours and then poured into 400 ml. of ice water. When no precipitate appeared, the solution was extracted with four 100 ml. portions of chloroform, and the extract was dried over anhydrous sodium sulfate. The chloroform was removed by evaporation in vacuo, leaving a solid residue and some acetic acid. The latter was removed by desiccation over sodium hydroxide at 0.2 mm. Hg. for four hours. The crude product was then recrystallized from ethanol, giving 17.7 g. (67 percent) of pale yellow crystals, m.p. 131°–134°C. A second recrystallization from ethanol gave the pure 4-hydroxy-6-methyl-3-propargylsulfinyl-2-pyrone as pale yellow needles, m.p. 133.5°–134.5°C.

Anal. Calcd. for $C_9H_8O_4S$: C, 50.93; H, 3.80; S, 15.11. Found: C, 50.80; H, 3.85; S, 14.8.

EXAMPLE 43

3-Cyclohexylmethylsulfinyl-4-hydroxy-6-methyl-2-pyrone

A solution, consisting of 6.00 g. (0.0236 mole) of 3-cyclohexylmethylthio-4-hydroxy-6-methyl-2-pyrone and 2.67 g. (0.0236 mole) of 30% hydrogen peroxide in 30 ml. of glacial acetic acid, was allowed to stand at room temperature for 26 hours, after which period of time it was poured into ice water, giving a white solid precipitate, which was collected on a filter and dried in vacuo over calcium chloride. The crude product weighed 5.8 g. (91 percent) and melted at 132.5°–133.5°C. Recrystallization from ethanol gave the pure 3-cyclohexylmethylsulfinyl-4-hydroxy-6-methyl-2-pyrone as white needles, m.p. 137°–138°C.

Anal. Calcd. for $C_{13}H_{18}O_4S$: C, 57.75; H, 6.71; S, 11.86. Found: C, 58.0; H, 6.62; S, 12.6.

EXAMPLE 44

3-Cyclohexylmethylsulfonyl-4-hydroxy-6-methyl-2-pyrone

A solution, consisting of 6.22 g. (0.0245 mole) of 3-cyclohexylmethylthio-4-hydroxy-6-methyl-2-pyrone and 10 g. (0.088 mole) of 30% hydrogen peroxide in 50 ml. of glacial acetic acid, was heated at 95°C. for 30 minutes, cooled and poured onto ice. The white, solid precipitate was collected on a filter and dried in vacuo over calcium chloride. The dry product weighed 6.0 g. (85 percent) and melted at 104°–105.5°C. Recrystallization from ethanol did not result in a higher melting point.

Anal. Calcd. for $C_{13}H_{18}O_5S$: C, 54.53; H, 6.34; S, 11.20. Found: C, 54.78; H, 6.27; S, 11.46.

EXAMPLE 45

4-Hydroxy-6-methyl-3-(2-phenylethylthio)-2-pyrone

To a solution of 10.1 g. (0.0800 mole) of 4-hydroxy-6-methyl-2-pyrone in 200 ml. of ethanol was added a solution of 3.20 g. (0.0800 mole) of sodium hydroxide in 125 ml. of water followed by 23.4 g. (0.0800 mole) of sodium hydroxide in 125 ml. of water followed by 23.4 g. (0.0800 mole) of 2-phenylethyl p-toluenethiolsulfonate. The mixture was heated under reflux with stirring for 15.5 hours, after which period of time the solvent was removed by evaporation in vacuo, and the residue shaken with water. The water suspension was then extracted with methylene chloride and the extract dried first over anhydrous sodium sulfate and then over anhydrous magnesium sulfate. The methylene chloride was removed by evaporation, and the brown, gummy residue was shaken with 100 ml. of 5% sodium hydroxide solution, the alkali-insoluble material being removed by extraction with methylene chloride and discarded. The aqueous alkaline phase was stirred with decolorizing charcoal at room temperature, filtered, cooled by means of an ice bath and acidified with dilute hydrochloric acid. A gum precipitated and crystallized with continued stirring. The crude product was collected on a filter and recrystallized from 2-propanol to give 6.8 g. (32 percent) of white crystals, m.p. 98.5°–101°C. A second recrystallization from 2-propanol gave the pure 4-hydroxy-6-methyl-3-(2-phenylethylthio)-2-pyrone as white crystals, m.p. 100.5°–101°C.

Anal. Calcd. for $C_{14}H_{14}O_3S$; C, 64.10; H, 5.38; S, 12.22. Found: C, 64.14; H, 5.48; S, 12.10.

EXAMPLE 46

3-tert.-Butylthio-4-hydroxy-6-methyl-2-pyrone

Ice (50g.) was added slowly with stirring to 175 g. of concentrated sulfuric acid, keeping the temperature below 35°C. by means of an ice-salt bath. The temperature of the diluted acid was adjusted to 5°C., and 38.6 g. (0.460 mole) of tert.-butyl alcohol was slowly added with stirring, keeping the temperature between 5° and 10°C. 4-Hydroxy-3-mercapto-6-methyl-2-pyrone (36.4 g., 0.230 mole) was then added with vigorous stirring over a period of about 15 minutes, keeping the temperature of the reaction mixture at 5°C. The cooling bath was then removed from the reaction vessel, and stirring was continued for one hour, 20 minutes, while the temperature of the reaction mixture rose to 24°C. The mixture was then poured into ice water, and the gummy precipitate crystallized to a gray solid (weight 42.4 g. (86 percent), m.p. 108.5°–112.5°C.) upon standing at room temperature overnight. The crude product was suspended in 200 ml. of water and then dissolved by the addition of 100 ml. of 10% sodium hydroxide solution. The solution was stirred at room temperature for one hour with decolorizing charcoal, filtered and acidified with with dilute hydrochloric acid. The cream-colored solid precipitate (37.7 g., m.p. 116.5°C.) was collected on a filter, washed with water and dried. Recrystallization from 2-propanol gave the pure 3-tert.-butylthio-4-hydroxy-6-methyl-2-pyrone as white crystals, m.p. 117°–117.5°C.

Anal. Calcd. for $C_{10}H_{14}O_3S$: C, 56.05; H, 6.59; S, 14.96. Found: C, 55.96; H, 6.71; S, 15.15.

EXAMPLE 47

3-tert.-Butylsulfinyl-4-hydroxy-6-methyl-2-pyrone

Hydrogen peroxide (30%, 5.29 g., 0.467 mole) was added in one portion to a solution of 10.0 g. (0.0467 mole) of 3-tert.-butylthio-4-hydroxy-6-methyl-2-pyrone in 85 ml. of glacial acetic acid. The solution was allowed to stand at room temperature for 66 hours and then was poured into ice water, resulting in the precipitation of the pure product as 8.9 g. (83 percent) of white crystals, m.p. 119°C.

Anal. Calcd. for $C_{10}H_{14}O_4S$: C, 52.16; H, 6.13; S, 13.92. Found: 52.06; H, 6.17; S, 13.97.

EXAMPLE 48

3-tert.-Butylsulfonyl-4--hyddroxy-6-methyl-2-pyrone

Hydrogen peroxide ((30%, 12 g.) was added to a solution of 6.50 g. (0.0303 mole) 3-tert.-butylthio-4-hydroxy-6-methyl-2-pyrone in 55 ml. of glacial acetic acid. The flask was heated on the steam bath for one hour, cooled and the reaction mixture poured into ice water, whereupon 2.6 g. of white crystalline solid precipitated. The solid was collected on a filter and air-dried; m.p. 118°–119°C.; weight 2.6 g. The filtrate was extracted with methylene chloride and the extract dried over anhydrous sodium sulfate and magnesium sulfate. The methylene chloride was removed by evaporation in vacuo, leaving 2.9 g. more product as white crystals, m.p. 118°–119.5°C. Recrystallization from ethanol gave the pure 3-tert.-butylsulfonyl-4-hydroxy-6-methyl-2-pyrone as white crystals, m.p. 119°–120°C.

Anal. Calcd. for $C_{10}H_{14}O_5S$: C, 48.77; H, 5.73; S, 13.02. Found: C, 48.50; H, 5.72; S, 13.15.

EXAMPLE 49

3-(p-Fluorobenzylsulfinyl)-4-hydroxy-6-methyl-2-pyrone

To a solution of 3-(p-fluorobenzylthio)-4-hydroxy-6-methyl-2-pyrone (10.0 g., 0.0376 mole) in glacial acetic acid (50 ml.) was added 30% hydrogen peroxide (4.3 g., 0.0376 mole). After standing for several days the solution was diluted with water, filtered and dried, yielding 6.4 g. (60 percent) of the desired product. Recrystallization from benzene yielded the pure product as a white solid, m.p. 127°–128°C.

Anal. Calcd. for $C_{13}H_{11}FO_4S$: C, 55.31; H, 3.93; S, 11.36. Found: C, 55.38; H, 3.92; S, 11.33.

EXAMPLE 50

4-Hydroxy-3-isobutylsulfinyl-6-methyl-2-pyrone

To a solution of 4-hydroxy-3-isobutylthio-6-methyl-2-pyrone (8.0 g., 0.0374 mole) in glacial acetic acid (50 ml.) was added 30% hydrogen peroxide (4.3 g., 0.0374 mole). The solution was allowed to stand for several days and then was diluted with water, filtered and the cake dried, yielding 8.2 g. (95 percent) of the desired product. Recrystallization from hexane gave the pure product as an off-white solid, m.p. 102°–103°C.

Anal. Calcd. for $C_{10}H_{14}O_4S$: C, 52.15; H, 6.13; S, 13.92. Found: C, 52.06; H, 6.20; S, 14.04.

EXAMPLE 51

3-(o-Fluorobenzylsulfinyl)-4-hydroxy-6-methyl-2-pyrone 3-(o-Fluorobenzylthio)-4-hydroxy-6-methyl-2-pyrone (13.8 g., 0.0519 mole) and 30% hydrogen peroxide (5.9 g., 0.0519 mole) were mixed with glacial acetic acid (100 ml.) with stirring. After ten days the peroxide had been consumed, and the solution was diluted with water. The resulting mixture was extracted with methylene chloride. The extract was dried ($MgSO_4$) and evaporated to dryness, leaving 13.3 g. (91 percent) of a colored solid. Recrystallization from a mixed hexane-benzene solution gave the pure product as a white solid, m.p. 115°–116°C.

Anal. Calcd. for $C_{13}H_{11}FO_4S$: C, 55.31; H, 3.93; S, 11.36. Found: C, 55.26; H, 4.18; S, 11.51.

EXAMPLE 52

3-(3,4-Dichlorobenzylsulfinyl)-4-hydroxy-6-methyl-2-pyrone 3-(3,4-Dichlorobenzylthio)-4-hydroxy-6-methyl-2-pyrone (12.0 g., 0.037 mole) and 40% peroxyacetic acid (7.2 g., 0.0378 mole) were dissolved in glacial acetic acid (200 ml.). After a day there was no peroxide left and a solid had crystallized. The mixture was diluted with water and extracted with methylene chloride. The extract was dried ($MgSO_4$) and evaporated to dryness leaving 11.9 g. (95 percent) of an off-white solid. Recrystallization from benzene gave the pure product as a white solid, m.p. 144°–146°C.

Anal. Calcd. for $C_{13}H_{10}Cl_2O_4S$: C, 46.86; H, 3.03. Found: C, 46.9; H, 3.11.

EXAMPLE 53

3-(2,4-Dichlorobenzylsulfinyl)-4-hydroxy-6-methyl-2-pyrone 3-(2,4-Dichlorobenzylthio)-4 -hydroxy-6-methyl-2-pyrone (13.0 g., 0.041 mole) and 40% peroxyacetic acid (7.8 g., 0.041 mole) were dissolved in glacial acetic acid (200 ml.). The solution was allowed to stand at room temperature for two weeks, then was diluted with water and extracted with methylene chloride. The extract was dried ($MgSO_4$) and evaporated to dryness, leaving 12.6 g. (93 percent) of an off-white solid. Recrystallization from benzene gave the pure product as white needles, m.p. 144°–146°C.

Anal. Calcd. for $C_{13}H_{10}Cl_2O_4S$: C, 46.86; H, 3.03. Found: C, 46.7; H, 3.07.

EXAMPLE 54

3-(m-Fluorobenzylsulfinyl)-4-hydroxy-6-methyl-2-pyrone 3-m-Fluorobenzylthio)-4-hydroxy-6-methyl-2-pyrone (6.0 g., 0.0265 mole) and 30% hydrogen peroxide (3.0 g., 0.0265 mole) were dissolved in glacial acetic acid (100 ml.) and allowed to stand at room temperature for four days. There was still peroxide remaining but the solution was diluted with water and extracted with methylene chloride. The methylene chloride extract was dried ($MgSO_4$) and evaporated to dryness leaving 5.9 g. (79 percent) of an off-white solid. Recrystallization from benzene gave a white solid that nmr and IR analysis indicated was a 1:1 mixture of the desired sulfoxide and the sulfone.

EXAMPLE 55

Ammonium salt of 3-benzylsulfinyl-4-hydroxy-6-methyl-2-pyrone

3-Benzylsulfinyl-4-hydroxy-6-methyl-2-pyrone (10.0 g., 0.0365 mole) was dissolved in concd. ammonium hydroxide (100 ml.). The solution was evaporated to dryness at 6 mm. pressure, keeping the temperature below 70°C. The residue was mixed with acetone from which the product slowly crystallized. The product was filtered and dried giving 4.4 g. (42 percent) of a white solid, m.p. 163°–164°C.

EXAMPLE 56

3-(p-Fluorobenzylsulfonyl)-4-hydroxy-6-methyl-2-pyrone

To a mixture of 3-(p-fluorobenzylthio)-4-hydroxy-6-methyl-2-pyrone(10.2 g., 0.0383 mole) in glacial acetic acid (50 ml.) was added 30% hydrogen peroxide (8.7 g., 0.0766 mole). The mixture was heated at reflux for 1.5 hours and diluted with water. The resulting mixture was filtered and dried, giving the desired product as 7.6 g. (53 percent) of a white solid. Recrystallization from benzene gave the pure product as a white solid, m.p. 180°–182°C.

Anal. Calcd. for $C_{13}H_{11}FO_5S$: C, 52.34; H, 3.72; S, 10.75. Found: C, 52.88; H, 3.77; S, 10.7.

EXAMPLE 57

4-Hydroxy-3-isobutylsulfonyl-6-methyl-2-pyrone

4-Hydroxy-3-isobutylthio-6-methyl-2-pyrone (8.0 g., 0.0374 mole) and 30% hydrogen peroxide (8.6 g., 0.0748 mole) were dissolved in glacial acetic acid (50 ml.) and heated at reflux for two hours. The solution was diluted with water, in which the product was soluble. The aqueous solution was extracted with methylene chloride. The extract was dried ($MgSO_4$) and evaporated to dryness, leaving 8.8 g. (96 percent) of the desired product. Recrystallization from benzene gave the pure product as white needles, m.p. 90°–91°C.

Anal. Calcd, for $C_{10}H_{14}O_5S$: C, 48.77; H, 5.73 S, 13.02. Found: $C_{48.7}$; H, 5.70; S, 13.29.

EXAMPLE 58

3-(3,4-Dichlorobenzylsulfonyl)-4-hydroxy-6-methyl-2-pyrone 3-(3,4-Dichlorobenzylthio)-4-hydroxy-6-methyl-2-pyrone (10.8 g., 0.034 mole) and 30% hydrogen peroxide (7.8 g., 0.068 mole) were dissolved in glacial acetic acid (100 ml.) and heated at reflux for two hours. The solution was diluted with water and extracted with methylene chloride. The methylene chloride extract was dried ($MgSO_4$) and evaporated to dryness, leaving 9.7 g. (82 percent) of an off-white solid. Recrystallization from benzene gave the pure compound as a white solid, m.p. 144°–145°C.

Anal Calcd, for $C_{13}H_{10}Cl_2O_5S$: C, 44.71; H, 2.89. Found: C, 44.9; H, 2.86.

EXAMPLE 59

4-Hydroxy-3-isobutylthio-6-methyl-2-pyrone

4-Hydroxy-6-methyl-2-pyrone (37.9 g., 0.3 mole), isobutyl methanethiolsulfonate (50.5 g., 0.3 mole), sodium hydroxide (12.0 g., 0.3 mole), water (100 ml.) and ethanol (200 ml.) were mixed and heated under reflux for 24 hours. The ethanol was removed under vacuum and the residue was mixed with water and extracted with chloroform. The extract was dried ($MgSO_4$) and the solvent removed by evaporation. The oily residue was crystallized from hexane, giving 21.5 g. (33 percent) of the pure product as a white fluffy solid, m.p. 106.5°–107.5°C.

Anal. Calcd. for $C_{10}H_{14}O_3S$: C, 56.06; H, 6.59; S, 14.96: Found: C, 56.34; H, 6.73; S, 12.59.

EXAMPLE 60

3-(o-Fluorobenzylthio)-4-hydroxy-6-methyl-2-pyrone

4-Hydroxy-3-mercapto-6-methyl-2-pyrone (49.5 g., 0.313 mole) and o-fluorobenzyl chloride (45.3 g., 0.313 mole) were dissolved in pyridine (250 ml.). The temperature rose from 20° to 43°C. The solution was heated at 90°C. for two hours, cooled and poured over ice and concd. hydrochloric acid (500 ml.). This mixture was extracted with methylene chloride. The extract was dried ($MgSO_4$) and evaporated to dryness, leaving an oily residue (80 g.) which is dissolved in hot benzene. Hexane was added to this hot benzene solution and an oil separated. The solution was decanted off. This was repeated until a solid separated. The mixture was cooled and filtered, giving 38.0 g. (46 percent) of the desired product. Recrystallization from benzene gave the pure product as a pale yellow solid, m.p. 123°–125°C.

Anal. Calcd, for $C_{13}H_{11}FO_3S$: C, 58.63; H, 4.16; S, 12.04. Found: C, 58.55; H, 4.24; S, 12.13.

EXAMPLE 61

3(2,4Dichlorobenzylthio)-4-hydroxy-6-methyl-2-pyrone

4-Hydroxy-3-mercapto-6-methyl-2-pyrone (47.5 g., 0.300 mole) and α2,4-trichlorotoluene (58.6 g., 0.300 mole) were dissolved in pyridine (250 ml.). The temperature rose from 20° to 43°C. The solution was then heated at 90°C. for two hours, cooled and poured onto ice and 500 ml. of concd. hydrochloric acid. The resulting mixture was extracted with methylene chloride. The extract was dried ($MgSO_4$) and the solvent removed by evaporation. The residue was mixed with hexane, filtered and dried, giving 53.3 g. (56 percent) of the desired product. Recrystallization from benzene gave the pure product as a white solid, m.p. 163°–164°C.

Anal. Calcd, for $C_{13}H_{10}Cl_2O_3S$: C, 49.22; H, 3.18; Cl, 22.36. Found: C, 49.35; H, 3.25; Cl, 22.10.

EXAMPLE 62

3-(m-Fluorobenzylthio)-4-hydroxy-6-methyl-2-pyrone

4-Hydroxy-3-mercapto-6-methyl-2-pyrone (50 g., 0.317 mole) and m-fluorobenzylchloride (45.8 g., 0.317 mole) were dissolved in pyridine (250 ml.). The temperature rose from 20° to 36°C. The resulting solution was heated at 90°C. for two hours and poured over ice and 500 ml. of concd. hydrochloric acid. This mixture was extracted with methylene chloride. The extract was dried ($MgSO_4$) and the solvent removed by evaporation. The residue was mixed with hexane, filtered and dried, yielding 44.6 g. (53 percent) of the desired product. Recrystallization from benzene gave the pure product as a white solid, m.p. 123.5°–124°C.

Anal. Calcd. for $C_{13}H_{11}FO_3S$: C, 58.63; H, 4.16; S, 12.04. Found: C, 58.32; H, 4.17; S, 12.12.

EXAMPLE 63

Ammonium salt of 4-hydroxy-3-isobutylthio-6-methyl-2-pyrone

4-Hydroxy-3-isobutylthio-6-methyl-2-pyrone (5.0 g., 0.023 mole) was dissolved in concd. ammonium hydroxide (100 ml.) and evaporated to dryness at 6 mm pressure, keeping the temperature below 70°C. The residue was mixed with acetone, filtered and dried, giving 4.0 g. (75 percent) of the pure product was a white solid, m.p. 163°–164°C.

EXAMPLE 64

3-(1-Adamantylthio)-4-hydroxy-6-methyl-2-pyrone

Ice (22 g.) was slowly added to 90 g. of concd. sulfuric acid with stirring, keeping the temperature below 35°C. by means of an ice-salt bath. 1-Adamantanol (18.2 g., 0.120 mole) was added followed by the slow addition of 15.8 g. (0.100 mole) of 4-hydroxy-3-mercapto-6-methyl-2-pyrone, keeping the temperature of the reaction mixture between 0° and 5°C. The ice bath was then removed from the reaction vessel, and the reaction mixture was warmed to 30°–40°C. with vigorous stirring for 1.5 hours. The mixture was then poured into ice water and allowed to stand for about 15 hours. The crude, solid product was collected on a filter, dried in vacuo over calcium chloride and recrystallized from ethanol (Darco) to give 8.3 g. (28 percent) of colorless needles, m.p. 175.5°–176.5°C. A second recrystallization from ethanol gave the pure product as colorless needles, m.p. 176°–177°C.

Anal. Calcd. for $C_{12}H_{20}O_3S$: C, 65.72; H, 6.90; S, 10.97. Found: C, 65.90; H, 6.90; S, 10.89.

EXAMPLE 65

3-(1-Adamantylsulfinyl)-4hydroxy-6-methyl-2-pyrone

To a solution of 2.0 g. (0.0068 mole) of 3-(1-adamantylthio)-4-hydroxy-6-methyl-2-pyrone in 50 ml. of glacial acetic acid was added 0.78 g. (0.0070 mole) of 30% hydrogen peroxide and the solution allowed to stand at room temperature for 19 hours. The solution was then poured into ice water, and the resulting white solid precipitate was collected on a filter and recrystallized from ethanol to give the pure product 3-(1-adamantylsulfinyl)-4-hydroxy-6-methyl-2-pyrone as 1.67 g. (80 percent) of colorless needles, m.p. 174.5°C.

Anal. Calcd. for $C_{16}H_{20}O_4S$: C, 62.31; H, 6.54; S, 10.40. Found: C, 62.44; H, 6.48; S, 10.55.

The compounds of the invention are employed as plant growth regulators for stunting plant, particularly grasses and including corn and wheat. Such stunting is advantageous to plant health and disease resistance. Stunting also facilitates mechanical harvesting. With corn and wheat, stunting prevents lodging.

Some of the compounds of the invention are also useful as antimicrobials, being effective against *Mycobacterium phlei, Staphylococcus aureus, Trichophyton mentagrophytes, Bacillus subtilis, Trichoderma species, Cephaloascus fragans, Candida albicans, Candida pelliculosa, Pullularia pullalans* and *Aspergillus terreous*. This is not to suggest that such compounds are equally effective against all such organisms or at the same concentrations.

Whether in use as plant growth regulators or as antimicrobials, the compounds can be employed in an unmodified form or dispersed on a finely divided solid and employed as dusts. Such mixtures can also be dispersed in water with or without the aid of a surface active-agent and the resulting aqueous suspensions employed as sprays. In other procedures, the products can be employed as active constituents in solvent solution, oil-in-water, or water-in-oil emulsions or aqueous dispersions. The augmented compositions are adapted to be formulated as concentrates and subsequently diluted with additional liquid or solid adjuvants to produce the ultimate treating compositions. Good results are obtained when employing compositions containing plant growth regulating or antimicrobial concentrations and usually from about 10 to about 10,000 parts by weight or one or more of the compounds per million parts of such composition for antimicrobial application and from about 2 to about 10 pounds per acre for pre-emergent application for plant growth stunting and from about 1,000 to about 5,000 parts per million for foliar application for plant growth stunting.

In the following Table, data are presented for plant growth stunting of various grasses, including wheat and corn, by conventional pre-emergent and foliar application for the indicated compounds of the examples. The data indicate percent growth reduction expressed as a percentage of normal growth controls.

Table I

| Plant Growth Stunting, % Reduction vs. Application Rate | | | |
|---|---|---|---|
| Pre-emergent Example | % Reduction/lb./acre | Foliar Example | % Reduction/ppm × 10³ |
| 9 | white winter wheat/30/5 corn/20/5 | 1 9 | cotton/10/4 cultured rice/40/1 |
| 10 | beans/60/10 | | sorghum/50/4 |
| 12 | beans/60/20 crabgrass/75/20 | 15 17 | cotton/20/4 soybeans/30/4 |
| 13 | corn/30/10 winter wheat/30/10 | | winter wheat/30/4 beans/50/4 |
| 16 | white winter wheat/15/10 | 19 | sorghum/20/4 |

Table I-continued

| Pre-emergent Example | Plant Growth Stunting, % Reduction vs. Application Rate % Reduction/lb./acre | Foliar Example | % Reduction/ppm × $10^3$ |
|---|---|---|---|
|  |  | 43 | sorghum/35/4 |
|  |  | 48 | cotton/30/4 |
| 18 | crabgrass/80/20 | 49 | crabgrass/90/4 |
|  | yellow foxtail/70/20 |  | yellow foxtail/50/4 |
| 19 | cultured rice/40/10 | 50 | sorghum/40/4 |
| 20 | soybeans/30/10 | 54 | sorghum/45/4 |
|  | cultured rice/30/2 | 55 | sorghum/50/4 |
| 21 | white winter wheat/30/2 |  | crabgrass/60/4 wild oats/50/4 |
|  | corn/20/2 | 56 | sorghum/20/4 |
| 22 | white winter wheat/40/2 | 59 | soybeans/30/2.5 sorghum/60/4 |
|  | corn/40/2 | 61 | crabgrass/80/4 |
| 24 | cotton/40/10 | 62 | sorghum/20/4 |
| 25 | cultured rice/30/10 | 63 | soybeans/40/5 |
| 26 | foxtail/100/20 |  | corn/30/2.5 |
| 27 | white winter wheat/50/20 | 65 | barnyard grass/40/4 |
|  | corn/50/2 |  |  |
|  | cultured rice/50/2 |  |  |
| 30 | corn/20/10 |  |  |
| 31 | corn/20/2 |  |  |
| 32 | cultured rice/30/5 white winter wheat/50/2 corn/50/2 |  |  |
| 33 | bindweed/100/20 |  |  |
| 35 | Johnson grass/100/20 |  |  |
| 36 | Johnston grass/100/20 barnyard grass/25/10 |  |  |
| 37 | cultured rice/50/10 yellow foxtail/70/10 |  |  |
| 38 | cultured rice/25/10 |  |  |
| 39 | yellow foxtail/75/10 crabgrass/50/10 |  |  |
| 40 | white winter wheat/40/2 corn/50/2 |  |  |
| 41 | white winter wheat/40/2 corn/30/2 |  |  |
| 42 | white winter wheat/30/10 corn/30/5 |  |  |
| 43 | white winter wheat/40/2 corn/40/2 |  |  |
| 44 | white winter wheat/30/2 corn/40/2 |  |  |
| 46 | wild oats/100/20 crabgrass/90/20 |  |  |
| 47 | wild mustard/100/20 crabgrass/40/20 |  |  |
| 49 | cultured rice/40/10 crabgrass/90/20 |  |  |
| 50 | cultured rice/20/10 crabgrass/90/20 |  |  |
| 51 | winter wheat/60/2 corn/27/2 cotton/37/2 |  |  |
| 52 | wild mustard/100/20 crabgrass/50/20 |  |  |
| 53 | crabgrass/70/20 wild oats/30/20 |  |  |
| 54 | cultured rice/10/10 crabgrass/80/20 |  |  |
| 55 | crabgrass/90/20 yellow foxtail/85/20 |  |  |
| 56 | cultured rice/10/10 crabgrass/60/20 |  |  |
| 57 | crabgrass/40/20 barnyard grass/40/20 |  |  |
| 58 | pigweeds/100/20 |  |  |
| 59 | cultured rice/70/10 Johnson grass/90/2 |  |  |
| 60 | crabgrass/50/20 yellow foxtail/75/20 |  |  |
| 62 | cultured rice/35/10 |  |  |
| 63 | cultured rice/20/10 white winter wheat/30/2 |  |  |
| 64 | yellow foxtail/40/20 barnyard grass/30/20 |  |  |

The following Table presents minimum growth inhibitory concentrations of the compounds of the indicated examples as determined by conventional agar dilution tests for the indicated bacteria, fungi and yeasts. At the indicated concentrations, no growth for the organisms was observed.

Table II

| Example | Mp* | Sa | Tm | Bs | T | Cf | Ca | Cp | Pp | At |
|---|---|---|---|---|---|---|---|---|---|---|
| 4 | 10 | | | | | | | | | |
| 10 | 10 | 100 | 10 | 10 | 500 | | | | | |
| 14 | 500 | 500 | 500 | | | | | | | |
| 16 | 500 | | | | | | | | | |
| 18 | | | 500 | | | | | | | |
| 19 | | | 500 | 500 | | | | | | |
| 21 | 500 | 500 | 500 | 500 | | | | | | |
| 25 | 100 | 500 | 500 | 500 | | 500 | | | | |
| 31 | 10 | 100 | 10 | 10 | | | 500 | 500 | 500 | |
| 34 | 10 | 100 | 500 | 10 | | | | | | |
| 45 | | | | | 500 | | | | | |
| 50 | | | 500 | | | | | | | |
| 61 | 500 | 500 | 500 | 500 | 500 | | | | 500 | |
| Controls no growth inhibition | | | | | | | | | | |

*Mp = *Mycobacterium phlei*
Sa = *Staphylococcus aureus*
Tm = *Trichophyton mentagrophytes*
Bs = *Bacillis subtilis*
T = *Trichoderma species*
Cf = *Cephaloascus fragans*
Ca = *Candida albicans*
Cp = *Candida pelliculosa*
Pp = *Pullularia pullulans*
At = *Aspergillus terreus*

What is claimed is:
1. A process for making a compound corresponding to the formula

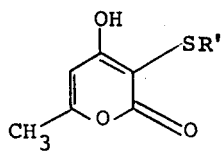

wherein R' represents a 1 to 20 carbon alkyl, phenyl, halophenyl, nitrophenyl, lower alkylphenyl, benzyl, phenethyl, naphthylmethyl, halobenzyl, lower alkylbenzyl, nitrobenzyl, propargyl, allyl, cyclohexyl loweralkyl, (lower alkylthio)-loweralkyl or adamantyl, which comprises reacting an alkali metal salt of 4-hydroxy-6-methyl-2-pyrone with a substantially equimolar proportion of an R'-thiolsulfonate of the formula $R^2$—$SO_2SR'$ wherein $R^2$ is methyl, phenyl or p-tolyl in the presence of an inert organic solvent at substantially reflux temperature; and recovering the said compound.

* * * * *